US007273846B2

(12) United States Patent
Bednarek

(10) Patent No.: US 7,273,846 B2
(45) Date of Patent: *Sep. 25, 2007

(54) SELECTIVE MELANIN-CONCENTRATING HORMONE TYPE-1 RECEPTOR AGONISTS

(75) Inventor: Maria A. Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 297 days.

This patent is subject to a terminal disclaimer.

(21) Appl. No.: 10/500,672

(22) PCT Filed: Jan. 6, 2003

(86) PCT No.: PCT/US03/00241

§ 371 (c)(1),
(2), (4) Date: Jul. 2, 2004

(87) PCT Pub. No.: WO03/060091

PCT Pub. Date: Jul. 24, 2003

(65) Prior Publication Data

US 2005/0020492 A1 Jan. 27, 2005

Related U.S. Application Data

(60) Provisional application No. 60/347,191, filed on Jan. 9, 2002.

(51) Int. Cl.
*C07K 7/08* (2006.01)
*A61K 38/00* (2006.01)
(52) U.S. Cl. .............................. 514/9; 514/13; 514/14; 514/15; 530/300; 530/326; 530/327; 530/334; 530/344; 435/7.1
(58) Field of Classification Search ................... 514/9, 514/13, 14, 15; 530/300, 326, 327, 334, 530/344; 435/7.1
See application file for complete search history.

(56) References Cited

U.S. PATENT DOCUMENTS

| 5,049,655 A | 9/1991 | Vaughan et al. |
| 5,849,708 A | 12/1998 | Maratos-Flier |

FOREIGN PATENT DOCUMENTS

| WO | WO 90/11295 | 10/1990 |
| WO | WO 01/57070 | 8/2001 |
| WO | WO 02/097037 | 12/2002 |

OTHER PUBLICATIONS

Audinot, V. et al. "Structure-Activity Relationship Studies of Melanin-concentrating Hormone (MCH)-related Peptide Ligands at SLC-1, the Human MCH Receptor", The Journal of Biological Chemistry, 2001, vol. 276, pp. 13554-13562.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Baker, B. et al. "Structure-Activity Studies With Fragments and Analogues of Salmonid Melanin-Concentrating Hormone", Peptides, 1990, vol. 11, pp. 1103-1108.
Bednarek, M. et al. "Short Segment of Human Melanin-Concentrating Hormone That Is Sufficient for Full Activation of Human Melanin-Concentrating Hormone Receptors 1 and 2", Biochemistry, 2001, vol. 40, pp. 9379-9386.
Bednarek, M. et al. "Synthesis and Biological Evaluation in Vitro of a Selective, High Potency Peptide Agonist of Human Melanin-concentrating Hormone Action at Human Melanin-concentrating Hormone Receptor 1", The Journal of Biological Chemistry, 2002, vol. 277, pp. 13821-13826.
Breton, C. et al. "Isolation and characterization of the human melanin-concentrating hormone gene and a variant gene", Molecular Brain Research, 1993, vol. 18, pp. 297-310.
Chambers, J. et al. "Melanin-concentrating hormone is the cognate ligand for the orphan G-protein-coupled receptor SLC-1", Nature, 1999, vol. 400, pp. 261-265.
Chimania, M. et al. "Predominant GABAB Mediated Dispersion of the Isolated Web Melanophores of the Indian Bull Frog, Rana Tigerina (Daud.)", Indian Journal of Pharmacology, 1995, vol. 27, pp. 241-244.
Drozdz, R. et al. "(D-(p-Benzoylphenylalanine)13, Tyrosine19)-Melanin-concentrating Hormone, a Potent Analogue for MCH Receptor Crosslinking", Journal of Peptide Science, 1999, vol. 5, pp. 234-242.
Drozdz, R. et al. "Melanin-concentrating hormone binding to mouse melanoma cells in vitro", FEBS Letters, 1995, vol. 359, pp. 199-202.
Erickson, J. et al. "Sensitivity to leptin and susceptibility to seizures of mice lacking neuropeptide Y", Nature, 1996, vol. 381, pp. 415-418.
Flier, J. et al. "Obesity and the Hypothalamus: Novel Peptides for New Pathways", Cell, 1998, vol. 92, pp. 437-440.
Hintermann, E. et al. "Synthesis and Characterization of New Radioligands for the Mammalian Melanin-Concentrating Hormone (MCH) Receptor", Journal of Receptor & Signal Transduction Research, 1999, vol. 19, pp. 411-422.
Kawauchi, H. et al. "Characterization of melanin-concentrating hormone in chum salmon pituitaries", Nature, 1983, vol. 305, pp. 321-323.
Knigge, K. et al. "Melanotropic Peptides in the Mammalian Brain: The Melanin-Concentrating Hormone", Peptides, 1996, vol. 17, pp. 1063-1073.
Lebl, M. et al. "Melanin Concentrating Hormone Analogues: Contraction of the Cyclic Structure. 1. Angonist Activity", Journal of Medicinal Chemistry, 1988, vol. 31, pp. 949-954.

(Continued)

*Primary Examiner*—Chih-Min Kam
(74) *Attorney, Agent, or Firm*—Catherine D. Fitch; Sheldon O. Heber

(57) ABSTRACT

The present invention features truncated hMCH analogs selectively active at MCH-1R over MCH-2R. Using amino acid numbering provided in hMCH, the featured analogs contain an $X^6$ which is either a D-amino acid, 5-guanidino-propionic acid or its lower or higher homolog, or a derivative thereof; and a $X^{10}$ which is either asparagine, glutamine, alanine, leucine, isoleucine, valine, norleucine, cyclohexylalanine, phenylalanine, (2')-naphthylalanine, tyrosine, histidine, tryptophan, lysine, serine, threonine, methionine, or a derivative thereof.

13 Claims, No Drawings

OTHER PUBLICATIONS

MacDonald, D. et al. "Molecular Characterization of the Melanin-Concentrating Hormone/Receptor Complex: Identification of Critical Residues Involved in Binding and Activation", Molecular Pharmacology, 2000, vol. 58, pp. 217-225.

Nahon, J. "The Melanin-Concentrating Hormone: From the Peptide to the Gene", Critical Reviews in Neurobiology, 1994, vol. 8, pp. 221-262.

Presse, F. et al. "Structure of the Human Melanin Concentrating Hormone mRNA", Molecular Endocrinology, 1990, vol. 4, pp. 632-637.

Qu, D. et al. "A role for melanin-concentrating hormone in the central regulation of feeding behaviour", Nature, 1996, vol. 380, pp. 243-247.

Sailer, A. et al. "Identification and characterization of a second melanin-concentrating hormone receptor, MCH-2R", Proc. Natl. Acad. Sci., USA, 2001, vol. 98, pp. 7564-7569.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Vaughan, J. et al. "Characterization of Melanin-Concentrating Hormone from Rat Hypothalamus", Endocrinology, 1989, vol. 125, pp. 1660-1665.

SELECTIVE MELANIN-CONCENTRATING HORMONE TYPE-1 RECEPTOR AGONISTS

CROSS-REFERENCE TO RELATED APPLICATIONS

The present application claims priority to provisional application U.S. Ser. No. 60/347,191, filed Jan. 9, 2002, hereby incorporated by reference herein.

BACKGROUND OF THE INVENTION

Neuropeptides present in the hypothalamus play a major role in mediating the control of body weight. (Flier et al., 1998, *Cell,* 92, 437-440.) Melanin-concentrating hormone (MCH) produced in mammals is a cyclic 19-amino acid neuropeptide synthesized as part of a larger pre-prohormone precursor in the hypothalamus which also encodes neuropeptides NEI and NGE. (Nahon et al., 1990, *Mol. Endocrinol.* 4, 632-637; Vaughan et al., U.S. Pat. No. 5,049,655; and Vaughan et al., 1989, *Endocrinology* 125, 1660-1665.) Human MCH (hMCH) has the following structure (SEQ. ID. NO. 1):

Asp-Phe-Asp-Met-Leu-Arg-Cys-Met-Leu-Gly-Arg-Val-Tyr-Arg-Pro-Cys-Trp-Gln-Val

MCH was first identified in salmon pituitary, and in fish MCH affects melanin aggregation thus affecting skin pigmentation. In trout and eels MCH has also been shown to be involved in stress induced or CRF-stimulated ACTH release. (Kawauchi et al., 1983, *Nature* 305, 321-323.) In humans two genes encoding hMCH have been identified that are expressed in the brain. (Breton et al., 1993, *Mol. Brain Res.* 18, 297-310.) In mammals MCH has been localized primarily to neuronal cell bodies of the hypothalamus which are implicated in the control of food intake, including perikarya of the lateral hypothalamus and zona inertia. (Knigge et al., 1996, *Peptides* 17, 1063-1073.)

Pharmacological and genetic evidence suggest that the primary mode of MCH action is to promote feeding (orexigenic). MCH mRNA is up regulated in fasted mice and rats, in the ob/ob mouse and in mice with targeted disruption in the gene for neuropeptide Y (NPY). (Qu et al., 1996, *Nature* 380, 243-247 and Erickson et al., 1996, *Nature* 381, 415-418.) Injection of MCH centrally (ICV) stimulates food intake and MCH antagonizes the hypophagic effects seen with a melanocyte stimulating hormone (αMSH). (Qu et al., 1996, *Nature* 380, 243-247.) MCH deficient mice are lean, hypophagic and have an increased metabolic rate. (Shimada et al., 1998, *Nature* 396, 670-673.) The administration of MCH has been indicated to be useful for promoting eating, appetite or the gain or maintenance of weight. (Maratos-Flier, U.S. Pat. No. 5,849,708.)

MCH action is not limited to modulation of food intake as effects on the hypothalamic-pituitary-axis have been reported. (Nahon, 1994, *Critical Rev. in Neurobiol.* 8, 221-262.) MCH may be involved in the body response to stress as MCH can modulate the stress-induced release of CRF from the hypothalamus and ACTH from the pituitary. In addition, MCH neuronal systems may be involved in reproductive or maternal function.

Human MCH can bind to at least two different receptors: MCH-1R and MCH-2R. (Chambers et al., 1999, *Nature* 400, 261-265; Saito et al., 1999, *Nature* 400, 265-269; Bächner et al., 1999, *FEBS Letters* 457:522-524; Shimomura et al., 1999, *Biochemical and Biophysical Research Communications* 261, 622-626; Sailer et al., *Proc. Natl. Acad. Sci.* 98:7564-7569, 2001.) The amino acid identity between MCH-2R and MCH-1R is about 38%. (Sailer et al., *Proc. Natl. Acad. Sci.* 98:7564-7569,2001.)

SUMMARY OF THE INVENTION

The present invention features truncated hMCH analogs selectively active at MCH-1R over MCH-2R. Using amino acid numbering provided in hMCH, the featured analogs contain an $X^6$ which is either a D-amino acid, 5-guanidinopropionic acid or its lower or higher homolog, or a derivative thereof; and a $X^{10}$ which is either asparagine, glutamine, alanine, leucine, isoleucine, valine, norleucine, cyclohexylalanine, phenylalanine, (2')-naphthylalanine, tyrosine, histidine, tryptophan, lysine, serine, threonine, methionine, or a derivative thereof.

Human MCH analogs selective for MCH-1R exert a greater activity at MCH-1R than at MCH-2R. MCH activities at MCH-1R and MCH-2R include receptor binding and receptor activation. MCH analogs selectively active at MCH-1R can have an increased binding, an increased activity, or both an increased binding and an increased activity at MCH-1R. Preferred MCH analogs have both an increased binding and an increased activity at MCH-1R. In different embodiments, the difference between the levels of activity at MCH-1R compared to MCH-2R is at least about 2, 5, 10, or 20 fold.

Thus, a first aspect of the present invention describes an optionally substituted peptide having the structure:

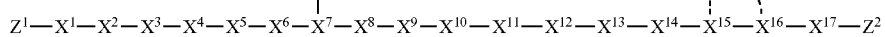

$$Z^1-X^1-X^2-X^3-X^4-X^5-X^6-X^7-X^8-X^9-X^{10}-X^{11}-X^{12}-X^{13}-X^{14}-X^{15}-X^{16}-X^{17}-Z^2$$

wherein $X^1$ is an optionally present amino acid that, if present, is either alanine, valine, leucine, isoleucine, proline, tryptophan, phenylalanine, methionine, glycine, seline, threonine, tyrosine, cysteine, asparagine, glutamine, lysine, arginine, histidine, aspartic acid, or glutamic acid, or a derivative thereof;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^6$ either is a D-amino acid, 5-guanidinopropionic acid or its lower or higher homolog, or a derivative thereof;

$X^7$ is either lysine, cysteine, homocysteine, 3-mercaptopropionic acid or its higher homolog, penicillamine, 2,3 diamino proprionic acid or its higher homolog, or aspartic acid or its higher homolog, or a derivative thereof;

$X^8$ is either methionine, norleucine, leucine, isoleucine, valine, methioninesulfoxide, or methioninesulfone, or a derivative thereof;

$X^9$ is either leucine, isoleucine, valine, alanine, methionine, or 5-aminopentanoic acid, or a derivative thereof;

$X^{10}$ is either asparagine, glutamine, alanine, leucine, isoleucine, valine, norleucine, cyclohexylalanine, phenylalanine, (2')-naphthylalanine, tyrosine, histidine, tryptophan, lysine, serine, threonine, methionine, or citrulline, or a derivative thereof;

$X^{11}$ is either arginine, lysine, citrulline, histidine, homoarginine, norarginine, or nitroarginine, or a derivative thereof;

$X^{12}$ is either valine, leucine, isoleucine, alanine, or methionine, or a derivative thereof;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof;

$X^{14}$ is either arginine, lysine, histidine, norarginine, homoarginine, nitroarginine, or 5-aminopentanoic acid, or a derivative thereof;

$X^{15}$ is either proline, alanine, valine, leucine, isoleucine, methionine, sarcosine, or 5-aminopentanoic acid, or a derivative thereof;

$X^{16}$ is an optionally present amino acid that if present is either cysteine, homocysteine, cysteamine, penicillamine, 2,3 diamino propionic acid or its higher homolog, or aspartic acid or its higher homolog, or a derivative thereof;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group;

provided that if $X^{16}$ is present, $X^{16}$ and $X^7$ together form a cyclic group joined by either a disulfide bond or an amide bond, wherein if $X^7$ is either cysteine, homocysteine, 3-mercaptopropionic acid or its higher homolog, or penicillamine, then $X^{16}$ is either cysteine, homocysteine, cysteamine, or penicillamine; if $X^7$ is 2,3 diamino proprionic acid or its higher homolog then $X^{16}$ is aspartic acid or its higher homolog; and if $X^7$ is aspartic acid or its higher homolog then $X^{16}$ is 2,3 diamino proprionic acid or its higher homolog;

further provided that if $X^{16}$ is not present, then $X^{17}$ is not present, $Z^2$ is not present, $X^7$ is lysine, and $X^{15}$ and $X^7$ together form a cyclic group joined by the $X^7$ Lys epsilon amino group and the $X^{15}$ carboxyl group;

or a labeled derivative of the peptide;

or a pharmaceutically acceptable salt of the peptide or of the labeled derivative.

Unless otherwise stated, those amino acids with a chiral center are provided in the L-enantiomer. Reference to "a derivative thereof" refers to the corresponding D-amino acid, N-alkyl-amino acid, β-amino acid, and ω-amino acid.

Another aspect of the present invention describes a method of screening for a compound able to bind MCH-1R. The method comprises the step of measuring the ability of the compound to affect binding of a hMCH analog to MCH-1R.

Another aspect of the present invention describes a method of selectively producing MCH-1R activity comprising the step of providing a cell functionally expressing MCH-1R with a hMCH analog. The method can be performed using cultured cells expressing MCH-1R or mammals.

Another aspect of the present invention features a method of screening for a MCH-1R antagonist. The method comprises the steps of:

a) combining together MCH-1R or a functional derivative thereof, a test compound, and a selectively active MCH-1R agonist, b) measuring the ability of the test compound to inhibit an MCH-1R activity as an indication of the ability of the test compound to act as a MCH-1R antagonist.

Another aspect of the present invention describes a method for increasing weight or appetite in a subject. The method comprises the step of administering to the subject an effective amount of a hMCH analog that activates MCH-1R to produce a weight increase.

Another aspect of the present invention describes a method for measuring the ability of a compound to decrease weight or appetite in a subject. The method involves administering to the subject an effective amount of a hMCH analog that would produce a weight or appetite increase and measuring the effect of the compound on weight or appetite.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

MCH-1R selective analogs were identified containing particular amino acids in position 6 and in position 10 of a truncated hMCH. Based on the identified amino acids different size MCH analogs can be provided. Preferred MCH analogs are smaller length analogs based on AC-hMCH6-16-NH$_2$ (SEQ. ID. NO. 2). AC-hMCH6-16-NH$_2$ provides a core region facilitating MCH-1R activity. Smaller length peptides offer advantages over larger peptides such as ease of synthesis and/or increased solubility in physiological buffers.

Preferred hMCH analogs have significant activity at MCH-1R. Significant activity at MCH-1R is activity that is at least about 50%, at least about 75%, or at least about 100% of activity compared to the activity obtained using hMCH. Activity at MCH-1R can be assayed using techniques measuring binding or G-protein activity such as those described in the Example provided below.

Uses of hMCH analogs include research tool and therapeutic applications. Research tool applications generally involve the use of a MCH analog and MCH-1R. MCH-1R can be present in different environments such as a mammalian subject, a whole cell, and membrane fragments. Examples of research tool applications of MCH analogs include screening for compounds active at MCH-1R, determining whether MCH-1R may be present in a sample or preparation, examining the role or effect of MCH and MCH-1R activation, and examining the role or effect of MCH antagonists.

Human MCH analogs selectivity active at MCH-1R have additional uses related to the selective activity. Examples of additional uses include being used to explore differences between MCH-1R and MCH-2R and to distinguish between the presence of MCH-1R and MCH-2R.

Human MCH analogs can be used to screen for both MCH agonists and MCH antagonists. Screening for MCH agonists can be performed, for example, by using a MCH analog in a competition experiment with test compounds. Screening for MCH antagonists can be performed, for example, by using a MCH analog to produce MCH-1R activity and then measuring the ability of a test compound to alter such activity.

Therapeutic applications of hMCH analogs involve administration to a subject containing an MCH-1R. Subjects possessing MCH-1R include humans, mice, rats, dogs, ferrets, and rhesus monkeys.

Reference to subject does not necessarily indicate the presence of a disease or disorder. The term subject includes, for example, humans being treated to help alleviate a disease or disorder, and humans being treated prophylactically to retard or prevent the onset of a disease or disorder.

MCH agonists can be used to achieve a beneficial effect in a subject. For example, a MCH agonist can be used to facilitate weight gain, maintenance of weight and/or appetite increase. Such effects are particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy, radiation therapy, and dialysis.

MCH antagonists can also be used to achieve a beneficial effect in a patient. For example, a MCH antagonist can be used to facilitate weight loss, appetite decrease, weight maintenance, cancer (e.g., colon or breast) treatment, pain reduction, stress reduction and/or treatment of sexual dysfunction.

MCH-1R Selectively Active Analogs

Selectively active hMCH analogs can be designed based on the disclosure provided herein concerning the importance of particular groups in positions 6 and 10 of hMCH. The remaining amino acids in a MCH analog can correspond to those amino acid present in naturally occurring MCH or can differ from the naturally occurring amino acids.

The importance of different MCH amino acids for providing MCH-1R activity is evaluated by references such as Bednarek et al., 2001, *Biochemistry* 40:9379-9386, Bednarek, International Publication No. WO 01/57070, and Audinot et al., 2001, *The Journal of Biological Chemistry* 276:13554-13562. Techniques described in these references can be employed to further evaluate amino acid alterations to MCH analogs.

Human MCH-1R analogs featured herein are optionally modified peptides having the structure:

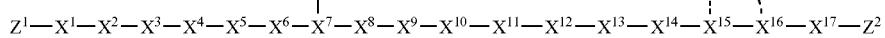

$$Z^1-X^1-X^2-X^3-X^4-X^5-X^6-X^7-X^8-X^9-X^{10}-X^{11}-X^{12}-X^{13}-X^{14}-X^{15}-X^{16}-X^{17}-Z^2$$

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^1$ if present is aspartic acid or glutamic acid; more preferably, $X^1$ if present is aspartic acid; and more preferably, $X^1$ is not present;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^2$ if present is phenylalanine or tyrosine; more preferably, $X^2$ if present is phenylalanine; and more preferably, $X^2$ is not present;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^3$ if present is aspartic acid or glutamic acid; more preferably, $X^3$ if present is aspartic acid; and more preferably, $X^3$ is not present;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or norleucine, or a derivative thereof; preferably, $X^4$ if present is methionine, leucine, isoleucine, valine, alanine or norleucine; more preferably, $X^4$ if present is methionine; and more preferably, $X^4$ is not present;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^5$ if present is leucine, methionine, isoleucine, valine or alanine; more preferably, $X^5$ if present is leucine; and more preferably, $X^5$ is not present;

$X^6$ either is a D-amino acid, 5-guanidinopropionic acid or its lower or higher homolog, or a derivative thereof; preferably, $X^6$ is either D-arginine, D-alanine, D-norleucine, D-α-aminobutyric acid, D-valine, D-leucine, D-isoleucine, D-proline, D-methionine, D-phenylalanine, D-asparagine, D-glutamine, D-serine, D-threonine, D-glutamic acid, D-aspartic acid, D-lysine, D-histidine, D-tryptophan, D-tyrosine, D-cyclohexylalanine, D-(2')naphthylalanine, D-ornithine, D-homoarginine, D-nitroarginine, D-norarginine, D-citrulline or 5-guanidinopropionic acid; more preferably $X^6$ is either D-arginine, D-alanine, D-norleucine, D-proline, D-phenylalanine, D-asparagine, D-serine, D-glutamic acid, D-lysine, or D-citrulline;

$X^7$ is either lysine, cysteine, homocysteine, 3-mercaptopropionic acid or its higher homolog, penicillamine, 2,3 diamino proprionic acid or its higher homolog, or aspartic acid or its higher homolog, or a derivative thereof; preferably, $X^7$ is either cysteine, homocysteine, 3-mercaptopropionic acid or its higher homolog, penicillamine, 2,3 diamino proprionic acid or its higher homolog, aspartic acid or its higher homolog, or a derivative thereof, more preferably, $X^7$ is cysteine, 2,3 diamino proprionic acid or aspartic acid;

$X^8$ is either methionine, norleucine, leucine, isoleucine, valine, methioninesulfoxide, or methioninesulfone, or a derivative thereof; preferably, $X^8$ is methionine, norleucine or N-methyl norleucine;

$X^9$ is either leucine, isoleucine, valine, alanine, methionine, or 5-aminopentanoic acid, or a derivative thereof; preferably, $X^9$ is leucine;

$X^{10}$ is either asparagine, glutamine, alanine, leucine, isoleucine, valine, norleucine, cyclohexylalanine, phenylalanine, (2')-naphthylalanine, tyrosine, histidine, tryptophan, lysine, serine, threonine, methionine, or citrulline, or a derivative thereof; preferably, $X^{10}$ is either asparagine or glutamine;

$X^{11}$ is either arginine, lysine, citrulline, histidine, homoarginine, norarginine, or nitroarginine, or a derivative thereof; preferably, $X^{11}$ is arginine;

$X^{12}$ is either valine, leucine, isoleucine, alanine, or methionine, or a derivative thereof; preferably, $X^{12}$ is valine;

$X^{13}$ is either phenylalanine, tyrosine, D-(p-benzoylphenylalanine), tryptophan, (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; or a derivative thereof; preferably, $X^{13}$ is phenylalanine, (2')napthylalanine, p-fluoro-phenylalanine, tyrosine, or cyclohexylalanine;

$X^{14}$ is either arginine, lysine, histidine, norarginine, homoarginine, nitroarginine, or 5-aminopentanoic acid, or a derivative thereof; preferably, $X^{14}$ is arginine;

$X^{15}$ is either proline, alanine, valine, leucine, isoleucine, methionine, sarcosine, or 5-aminopentanoic acid, or a derivative thereof; preferably, $X^{15}$ is proline or sarcosine;

$X^{16}$ is an optionally present amino acid that if present is either cysteine, homocysteine, cysteamine, penicillamine, 2,3 diamino propionic acid or its higher homolog, or aspartic acid or its higher homolog, or a derivative thereof; preferably, $X^{16}$ is present; more preferably, $X^{16}$ is either cysteine, D-cysteine, aspartic acid, or diamino proprionic acid; more preferably, $X^{16}$ is cysteine or D-cysteine;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^{17}$ if present is tyrosine or tryptophan; more preferably, $X^{17}$ is not present;

$Z^1$ is an optionally present protecting group that, if present, is covalently joined to the N-terminal amino group;

$Z^2$ is an optionally present protecting group that, if present, is covalently joined to the C-terminal carboxy group;

provided that if $X^{16}$ is present, $X^{16}$ and $X^7$ together form a cyclic group joined by either a disulfide bond or an amide bond, wherein if $X^7$ is either cysteine, homocysteine, 3-mercaptopropionic acid or its higher homolog, or penicillamine, then $X^{16}$ is either cysteine, homocysteine, cystearine, or penicillamine; if $X^7$ is 2,3 diamino proprionic acid or its higher homolog then $X^{16}$ is aspartic acid or its higher homolog, and if $X^7$ is aspartic acid or its higher homolog then $X^{16}$ is 2,3 diamino proprionic acid or its higher homolog; preferably the cyclic group is from 32-36 atoms, more preferably it is 32 atoms;

further provided that if $X^{16}$ is not present, then $X^{17}$ is not present, $Z^2$ is not present, $X^7$ is lysine, and $X^{15}$ and $X^7$ together form a cyclic group joined by the $X^7$ Lys epsilon amino group and the $X^{16}$ carboxyl group;

or a labeled derivative of the peptide;

or a pharmaceutically acceptable salt of the peptide or of the labeled derivative.

The present invention comprehends diastereomers as well as their racemic and resolved enantiomerically pure forms. hMCH analogs can contain D-amino acids, L-amino acids, or a combination thereof.

In different embodiments, hMCH analogs contain a preferred (or more preferred) group at one or more different locations. More preferred embodiments contain preferred (or more preferred) groups in more of the different locations.

A protecting group covalently joined to the N-terminal amino group reduces the reactivity of the amino terminus under in vivo conditions. Amino protecting groups include optionally substituted —$C_{1-10}$ alkyl, optionally substituted —$C_{2-10}$ alkenyl, optionally substituted aryl, —$C_{1-6}$ alkyl optionally substituted aryl, —C(O)—$(CH_2)_{1-6}$—COOH, —C(O)—$C_{1-6}$ alkyl, —C(O)-optionally substituted aryl, —C(O)—O-$C_{1-6}$ alkyl, and —C(O)—O-optionally substituted aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

A protecting group covalently joined to the N-terminal amino group reduces the reactivity of the amino terminus under in vivo conditions. Amino protecting groups include optionally substituted —$C_{1-10}$ alkyl, optionally substituted —$C_{2-10}$ allcenyl, optionally substituted aryl, —$C_{1-6}$ alkyl optionally substituted aryl, —C(O)—$(CH_2)_{1-6}$—COOH, —C(O)—$C_{1-6}$ alkyl, —C(O)-optionally substituted aryl, —C(O)—O-$C_{1-6}$ alkyl, and —C(O)—O-optionally substituted aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

"Alkyl" refers to an optionally substituted hydrocarbon, or optionally substituted hydrocarbon group joined by carbon-carbon single bonds. The alkyl hydrocarbon group may be straight-chain or contain one or more branches or cyclic groups. Preferably, the alkyl group is 1 to 4 carbons in length. Examples of alkyl include methyl, ethyl, propyl, isopropyl, cyclopropyl, butyl, and t-butyl. Alkyl groups may be substituted with one or more substituents selected from the group consisting of halogen (preferably —F or —Cl), —OH, —CN, —SH, —NH$_2$, —NO$_2$, —C$_{1-2}$ alkyl substituted with 1 to 6 halogens (preferably —F or —Cl, more preferably —F), —CF$_3$, —OCH$_3$, or —OCF$_3$. In different embodiments the alkyl has none or one substituent.

"Alkenyl" refers to an optionally substituted hydrocarbon group containing one or more carbon-carbon double bonds. The alkenyl hydrocarbon group may be straight-chain or contain one or more branches or cyclic groups. Preferably, the alkenyl group is 2 to 4 carbons in length. Alkenyl groups may be substituted with one or more substituents selected from the group consisting of halogen (preferably —F or —Cl), —OH, —CN, —SH, —NH$_2$, —NO$_2$, —C$_{1-2}$ alkyl substituted with 1 to 5 halogens (preferably —F or —Cl, more preferably —F), —CF$_3$, —OCH$_3$, or —OCF$_3$. In different embodiments the alkenyl has none or one substituent.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring, more preferably benzyl. Aryl groups may be substituted with one or more substituents selected from the group consisting of —C$_{1-4}$ alkyl, —C$_{1-4}$ alkoxy, halogen (preferably —F or —Cl), —OH, —CN, —SH, —NH$_2$, —NO$_2$, —C$_{1-2}$ alkyl substituted with 1 to 5 halogens (preferably —F or —Cl, more preferably —F), —CF$_3$, or —OCF$_3$. In different embodiments the aryl group has three, two, one, or zero, substituents.

A labeled derivative indicates the presence of a detectable label. Examples of detectable labels include luminescent, enzymatic, and radioactive labels. A preferred radiolabel is $^{125}$I. Both the type of label and the position of the label can affect MCH activity. Labels should be selected so as not to substantially alter the activity of the MCH analog at MCH-LR. The effect of a particular label on MCH activity can be determined using assays measuring MCH activity and/or binding.

In preferred embodiments $X^{16}$ is present, $X^{17}$ is optionally present and the optionally modified peptide has the structure:

Production of Human MCH analogs

Human MCH analogs can be produced using techniques well known in the art. For example, a polypeptide region of a MCH analog can be chemically or biochemically synthesized and, if desired, modified to produce a blocked N-terminus and/or blocked C-terminus. Techniques for chemical synthesis of polypeptides are well known in the art. (See e.g., Vincent, *Peptide and Protein Drug Delivery*, New York, N.Y., Dekker, 1990.) Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989.

MCH-1R

MCH-1R is a G-protein coupled receptor that responds to hMCH. Functional MCH-1R activity can be produced using naturally occurring human MCH-1R and functional derivatives thereof. Naturally occurring MCH-1R and functional derivatives thereof are activated by HMCH and can be identified by the presence of at least 12 contiguous amino acids as that present in human MCH-1R of SEQ. ID. NO. 35.

Reference to at least 12 contiguous amino acids present in SEQ. ID. NO. 35 provides a tag for an MCH-1R functional derivative. In different embodiments, functional derivatives comprise at least about 30 consecutive amino acids present in SEQ. ID. NO. 35, or comprise or consist of SEQ. ID. NO. 35.

In an embodiment of the present invention the MCH-1R is a mammalian MCH-1R. Examples of mammalian MCH-1R include MCH-1R found a human, ferret, mouse, rat, dog, and rhesus monkey.

MCH-1R derivatives can be produced, for example, by starting with human MCH-1R. Functional derivatives of MCH-1R can be produced, for example, by introducing amino acid substitutions, additions and deletions. The ability of a polypeptide to have MCH-1R activity can be confirmed using techniques such as those measuring G-protein activity.

Differences in naturally occurring amino acids are due to different R groups. An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

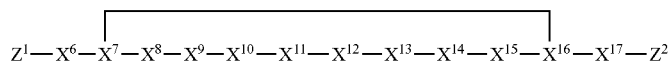

wherein the different groups, and preferred groups, are as described above. More preferred embodiments can be produced having different combinations and numbers of preferred and/or more preferred groups.

Changes outside of different amino acid groups can also be made. Preferably, such changes are made taking into account the position of the amino acid to be substituted in the polypeptide. For example, arginine can substitute more freely for nonpolor amino acids in the interior of a polypeptide then glutamate because of its long aliphatic side chain. (See, Ausubel, *Current Protocols in Molecular Biology*, John Wiley, 1987-1998, Supplement 33 Appendix 1C.)

MCH Receptor Binding Assay

Assays measuring the ability of a compound to bind to MCH-1R employ a MCH-1R polypeptide comprising a hMCH binding site. MCH-1R polypeptides include full-length human MCH-1R and functional derivatives thereof, MCH-1R fragments containing the MCH binding site, and chimeric polypeptides comprising such MCH-1R fragments. A chimeric polypeptide comprising a MCH-1R fragment that binds hMCH also contains one or more polypeptide regions not found in a naturally occurring MCH-1R. Preferably, assays measuring MCH binding employ full length MCH-1R of SEQ. ID. NO. 35.

The MCH-1R amino acid sequence involved in hMCH binding can be identified using labeled hMCH or hMCH analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding hMCH can be subdivided or mutated to further locate the hMCH binding region. Fragments used for binding studies can be generated using recombinant nucleic acid techniques.

Binding assays can be performed using individual compounds or preparations containing different numbers of compounds. A preparation containing different numbers of compounds having the ability to bind to the MCH-1R can be divided into smaller groups of compounds that can be tested to identify the compound(s) binding to the receptor. In an embodiment of the present invention a test preparation containing at least 10 compounds is used in a binding assay.

Binding assays can be performed using recombinantly produced MCH-1R polypeptides present in different environments. Such environments include, for example, cell extracts and purified cell extracts containing a MCH-1R polypeptide expressed from recombinant nucleic acid or naturally occurring nucleic acid; and also include, for example, the use of a purified MCH-1R produced by recombinant means or from naturally occurring nucleic acid which is introduced into a different environment.

Screening for MCH-1R Active Compounds

Screening for MCH-1R active compounds is facilitated using recombinant nucleic acid expressing a polypeptide having MCH-1R activity. Recombinantly expressed receptors offers several advantages in screening for receptor active compounds, such as the ability to express the receptor in a defined cell system so that responsiveness to receptor active compounds can more readily be differentiated from responses to other receptors. For example, MCH-1R can be expressed in a cell line such as HEK 293, COS 7, and CHO using an expression vector, wherein the same cell line without the expression vector can act as a control.

A recombinant "nucleic acid" refers to an artificial combination of two or more nucleotide sequence regions. The artificial combination is not found in nature. Recombinant nucleic acid includes nucleic acid having a first coding region and a regulatory element or a second coding region not naturally associated with the first coding region. Preferred recombinant nucleotide sequences are those where a coding region is under the control of an exogenous promoter, and where a second coding region is a selectable marker. The recombinant nucleotide sequence can be present in a cellular genome or can be part of an expression vector.

Preferably, expression is achieved in a host cell using an expression vector. An expression vector contains recombinant nucleic acid encoding a polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Screening for MCH-1R active compounds is facilitated through the use of a hMCH analog in the assay. The MCH analog provides for MCH-1R activity. The effect of test compounds on such activity can be measured to identify, for example, allosteric modulators and antagonists. Additionally, such assays can be used to identify agonists.

MCH Receptor Activity

MCH-1R and MCH-2R are G protein coupled receptors. MCH-1R couples to both Gi and Gq, while MCH-2R couples to Gq. Coupling of Gi results in the inhibition of adenylate cyclase and subsequent reductions in cAMP levels. Coupling to Gq leads to activation of phospholipase C and subsequent elevation of intracellular $Ca^{2+}$.

Techniques for measuring different G-protein activities, such as Gi, Gs, and Gq are well known in the art. Gi and Gs activity can be measured using techniques such as a melonaphore assay, assays measuring cAMP production, assays measuring inhibition of cAMP accumulation, and assays measuring binding of $^{35}$S-GTP. cAMP can be measured using different techniques such as a radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is BEK293/aeql7. (Button et al., 1993, *Cell Calcium* 14, 663-671, and Feighner et al., 1999, *Science* 284, 2184-2188, both of which are hereby incorporated by reference herein.)

Chimeric receptors containing a hMCH binding region functionally coupled to a G protein can also be used to measure MCH receptor activity. A chimeric MCH receptor contains an N-terminal extracellular domain; a transmembrane domain made up of transmembrane regions, extracellular loop regions, and intracellular loop regions; and an intracellular carboxy terminus. Techniques for producing chimeric receptors and measuring G protein coupled responses are provided for in, for example, International Application Number WO 97/05252, and U.S. Pat. No. 5,264,565.

Weight or Appetite Alteration

Human MCH analogs can be used in methods to increase or maintain weight and/or appetite in a subject. Such methods can be used, for example, as part of an experimental protocol examining the effects of MCH antagonists to achieve a beneficial effect in a subject or to further examine the physiological effects of MCH.

Experimental protocols examining the effects of MCH antagonists can be performed, for example, by using a sufficient amount of a hMCH analog to produce a weight or appetite increase in a subject and then examining the effect of a test compound. Changes in weight and appetite can be measured using techniques well known in the art.

Increasing weight or appetite can be useful for maintaining weight or producing a weight or appetite gain in an under weight subject, or in a patient having a disease or undergoing treatment that affects weight or appetite. In addition, for example, farm animals possessing MCH-1R can be treated to gain weight.

Under weight subjects include those having a body weight about 10% or less, 20% or less, or 30% or less, than the lower end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19-22.

Administration

Human MCH analogs can be formulated and administered to a subject using the guidance provided herein along with techniques well known in the art. The preferred route of administration ensures that an effective amount of compound reaches the target. Guidelines for pharmaceutical administration in general are provided in, for example, Remington's Pharmaceutical Sciences 18$^{th}$ Edition, Ed. Gennaro, Mack Publishing, 1990, and Modern Pharmaceutics 2$^{nd}$ Edition, Eds. Banker and Rhodes, Marcel Dekker, Inc., 1990, both of which are hereby incorporated by reference herein.

Human MCH analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Human MCH analogs can be administered using different routes such as by injection. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Human MCH analogs can be provided in kit. Such a kit typically contains an active compound in dosage forms for administration. A dosage form contains a sufficient amount of active compound such that a weight or appetite increase can be obtained when administered to a subject during regular intervals, such as 1 to 6 times a day, during the course of 1 or more days. Preferably, a kit contains instructions indicating the use of the dosage form for weight or appetite increase and the amount of dosage form to be taken over a specified time period.

EXAMPLES

Examples are provided below to further illustrate different features of the present invention. The examples also illustrate useful methodology for practicing the invention. These examples do not limit the claimed invention.

Example 1

MCH Receptor Sequences

Human MCH-1R and MCH-2R amino acid and encoding cDNA sequences are as follows:

```
MCH-1R Amino Acid Sequence
MDLEASLLPTGPNASNTSDGPDNLTSAGSPPR  (SEQ. ID. NO. 35)

TGSISYINIIMPSVFGTICLLGIIGNSTVIFA

VVKKSKLHWCNNVPDIFIINLSVVDLLFLLGM

PFMIHQLMGNGVWHFGETMCTLITAMDANSQF

TSTYILTAMAIDRYLATVHPISSTKFRKPSVA

TLVICLLWALSFISITPVWLYARLIPFPGGAV

GCGIRLPNPDTDLYWFTLYQFFLAFALPFVVI

TAAYVRILQRMTSSVAPASQRSIRLRTKRVTR

TAIAICLVFFVCWAPYYVLQLTQLSISRPTLT

FVYLYNAAISLGYANSCLNPFVYIVLCETFRK

RLVLSVKPAAQGQLRAVSNAQTADEERTESKG

T

MCH-1R cDNA Sequence
ATGGACCTGGAAGCCTCGCTGCTGCCCACTGG  (SEQ. ID. NO. 36)

TCCCAACGCCAGCAACACCTCTGATGGCCCCG

ATAACCTCACTTCGGCAGGATCACCTCCTCGC

ACGGGGAGCATCTCCTACATCAACATCATCAT

GCCTTCGGTGTTCGGCACCATCTGCCTCCTGG

GCATCATCGGGAACTCCACGGTCATCTTCGCG

GTCGTGAAGAAGTCCAAGCTGCACTGGTGCAA

CAACGTCCCCGACATCTTCATCATCAACCTCT
```

-continued

```
CGGTAGTAGATCTCCTCTTTCTCCTGGGCATG

CCCTTCATGATCCACCAGCTCATGGGCAATGG

GGTGTGGCACTTTGGGGAGACCATGTGCACCC

TCATCACGGCCATGGATGCCAATAGTCAGTTC

ACCAGCACCTACATCCTGACCGCCATGGCCAT

TGACCGCTACCTGGCCACTGTCCACCCCATCT

CTTCCACGAAGTTCCGGAAGCCCTCTGTGGCC

ACCCTGGTGATCTGCCTCCTGTGGGCCCTCTC

CTTCATCAGCATCACCCCTGTGTGGCTGTATG

CCAGACTCATCCCCTTCCCAGGAGGTGCAGTG

GGCTGCGGCATACGCCTGCCCAACCCAGACAC

TGACCTCTACTGGTTCACCCTGTACCAGTTTT

TCCTGGCCTTTGCCCTGCCTTTTGTGGTCATC

ACAGCCGCATACGTGAGGATCCTGCAGCGCAT

GACGTCCTCAGTGGCCCCCGCCTCCCAGCGCA

GCATCCGGCTGCGGACAAAGAGGGTGACCCGC

ACAGCCATCGCCATCTGTCTGGTCTTCTTTGT

GTGCTGGGCACCCTACTATGTGCTACAGCTGA

CCCAGTTGTCCATCAGCCGCCCGACCCTCACC

TTTGTCTACTTATACAATGCGGCCATCAGCTT

GGGCTATGCCAACAGCTGCCTCAACCCCTTTG

TGTACATCGTGCTCTGTGAGACGTTCCGCAAA

CGCTTGGTCCTGTCGGTGAAGCCTGCAGCCCA

GGGGCAGCTTCGCGCTGTCAGCAACGCTCAGA

CGGCTGACGAGGAGAGGACAGAAAGCAAAGGC

ACCTGA
```

MCH-2R Amino Acid Sequence
```
MNPFHASCWNTSAELLNKSWNKEFAYQTASVV    (SEQ. ID. NO. 37)

DTVILPSMIGIICSTGLVGNILIVFTIIRSRK

KTVPDIYICNLAVADLVHIVGMPFLIHQWARG

GEWVFGGPLCTIITSLDTCNQFACSAIMTVMS

VDRYFALVQPFRLTRWRTRYKTIRINLGLWAA

SFILALPVWVYSKVIKFKDGVESCAFDLTSPD

DVLWYTLYLTITTFFFPLPLILVCYILILCYT

WEMYQQNKDARCCNPSVPKQRVMKLTKMVLVL

VVVFILSAAPYHVIQLVNLQMEQPTLAFYVGY

YLSICLSYASSSINPFLYILLSGNFQKRLPQI

QRRATEKEINNMGNTLKSHF
```

MCH-2R cDNA Sequence (SEQ. ID. NO. 38)
```
ATGAATCCATTTCATGCATCTTGTTGGAACAC

CTCTGCCGAACTTTTAAACAAATCCTGGAATA

AAGAGTTTGCTTATCAAACTGCCAGTGTGGTA

GATACAGTCATCCTCCCTTCCATGATTGGGAT

TATCTGTTCAACAGGGCTGGTTGGCAACATCC

TCATTGTATTCACTATAATAAGATCCAGGAAA

AAAACAGTCCCTGACATCTATATCTGCAACCT

GGCTGTGGCTGATTTGGTCCACATAGTTGGAA

TGCCTTTTCTTATTCACCAATGGGCCCGAGGG

GGAGAGTGGGTGTTTGGGGGGCCTCTCTGCAC

CATCATCACATCCCTGGATACTTGTAACCAAT

TTGCCTGTAGTGCCATCATGACTGTAATGAGT

GTGGACAGGTACTTTGCCCTCGTCCAACCATT

TCGACTGACACGTTGGAGAACAAGGTACAAGA

CCATCCGGATCAATTTGGGCCTTTGGCAGCT

TCCTTTATCCTGGCATTGCCTGTCTGGGTCTA

CTCGAAGGTCATCAAATTTAAAGACGGTGTTG

AGAGTTGTGCTTTTGATTTGACATCCCCTGAC

GATGTACTCTGGTATACACTTTATTTGACGAT

AACAACTTTTTTTTTCCCTCTACCCTTGATTT

TGGTGTGCTATATTTTAATTTTATGCTATACT

TGGGAGATGTATCAACAGAATAAGGATGCCAG

ATGCTGCAATCCCAGTGTACCAAAACAGAGAG

TGATGAAGTTGACAAAGATGGTGCTGGTGCTG

GTGGTAGTCTTTATCCTGAGTGCTGCCCCTTA

TCATGTGATACAACTGGTGAACTTACAGATGG

AACAGCCCACACTGGCCTTCTATGTGGGTTAT

TACCTCTCCATCTGTCTCAGCTATGCCAGCAG

CAGCATTAACCCTTTTCTCTACATCCTGCTGA

GTGGAAATTTCCAGAAACGTCTGCCTCAAATC

CAAAGAAGAGCGACTGAGAAGGAAATCAACAA

TATGGGAAACACTCTGAAATCACACTTTTAG
```

Example 2

Synthesis of Human MCH Analogs

Human MCH analogs were produced using the procedures described below and varying the stepwise addition of amino acid groups. Other procedures for producing and modifying peptides are well known in the art.

Elongation of peptide chains on 4-(2',4'-dimethoxyphenyl-Fmoc-aminomethyl)-phenoxy resin (0.65 meq/g substitution) was performed with a 431A ABI peptide synthesizer.

Manufacture-supplied protocols were applied for coupling of the hydroxybenzotriazole esters of amino acids in N-methylpyrrolidone (NMP). The fluorenylmethyloxycarbonyl (Fmoc) group was used for the semipermanent protection of α-amino groups, whereas the side chains were protected with: tert-butyl for aspartic acid and tyrosine residue, 2,2,4,6,7-pentamethyldihydrobenzofuran-5-sulfonyl (Pbf) for arginine, and trityl for cysteine.

Peptides were cleaved from the resin with TFA containing 5% of anisole. After 2 hours at room temperature the peptidyl resin was filtered, washed with TFA and the combined filtrates were evaporated to dryness in vacuo. The residue was triturated with ether, the precipitate which formed was filtered, washed with ether, and dried. The crude peptides were dissolved in 5% acetic acid in water, and the pH of the solutions were adjusted to pH about 8.2 with dilute ammonium hydroxide. The reaction mixtures were stirred vigorously while a 0.05% solution of potassium ferricyanide ($K_3Fe(CN)_6$) in water was added dropwise till the solution remained yellow for about 5 minutes. After an additional 20 minutes, oxidation was terminated with ca. 1 ml of acetic acid and the reaction mixtures were lyophilized.

The lyophilized crude peptides were analyzed by analytical reverse-phase high-pressure liquid chromatography (RP HPLC) on a C18 Vydac column attached to a Waters 600E system with automatic Wisp 712 injector and 991 Photodiode Array detector. A standard gradient system of 0-100% buffer B in 30 minutes was used for analysis: buffer A was 0.1% trifluoroacetic acid in water and buffer B was 0.1% triflouroacetic acid in acetonitrile. HPLC profiles were recorded at 210 nm and 280 nm. Preparative separations were performed on a Waters Delta Prep 4000 system with a semipreparative C18 RP Waters column. The above-described solvent system of water and acetonitrile, in a gradient of 0-70% buffer B in 60 minutes, was used for separation. The chromatographically homogenous products (purity>97%) were analyzed by electrospray mass spectrometry.

Example 3

Radioligand Binding Assays

Membrane binding assays were performed on transiently-transfected COS-7 cells expressing human MCH-2R from the plasmid vector pCI-neo (Promega, Madison, Wis.), on a Chinese hamster ovary (CHO) cell line stably expressing the MCH-2R from the plasmid vector pEF1/V5-HisB (Invitrogen, Carlsbad, Calif.), or a CHO cell line stably expressing human MCH-1R from pcDNA3.1. For transient expression, COS-7 cells were cultured in Dulbecco's modified Eagle medium (Gibco BRL, Rockville, Md.) with 10% heat inactivated fetal calf serum.

A suspension of $7\times10^6$ COS-7 cells were transfected with 20 μg of pCI-neo/MCH-2R plasmid by electroporation and cells were harvested after 60-72 hours. Membranes were prepared from transient and stable transfectants by hypotonic lysis, frozen in liquid nitrogen, and stored at −80° C.

A scintillation proximity assay (SPA) was developed to measure the specific binding of $[^{125}I]$-$[Phe^{13}Tyrl^{9}]$-hMCH. (Bednarek et al., 2001, *Biochemistry* 40:9379-9386.) SPA's were carried out using wheat-germ agglutinin-polyvinyltoluene beads (Amersham Corp., Arlington Heights, Ill.), in 96-well OptiPlates (Packard, Meriden, Conn.). Each well contained 0.25 mg of SPA beads, 1-10 μg of membrane protein, and 200 μl of binding buffer (50 mM Tris pH 7.4, 10 mM $MgCl_2$, 2 mM EDTA, 12% glycerol, 0.1% BSA). Binding buffer contained 50 mM Tris pH 7.4, 8 MM $MgCl_2$, 12% glycerol, 0.1% BSA (Sigma, St. Louis, Mo.) and protease inhibitors: 4 μg/ml of leupeptin (Sigma, St. Louis, Mo.), 40 μg/ml of Bacitracin (Sigma, St. Louis, Mo.), 5 μg/ml of Aprotinin (Roche Molecular Biochem., Indianapolis, Ind.), 0.05M AEBSF (Roche Molecular Biochem., Indianapolis, Ind.), and mM Phosphoramidon (Boeringer Mannheim)). Assays were optimized with respect to membrane preparations: for CHO/MCH-1R membranes, 1 μg of membranes per well yielded a>6× specific binding window and for COS or CHO MCH-2R membranes, 8 μg of membrane protein yielded a window of about 3×.

Specific binding is defined as the difference between total binding and non-specific binding conducted in the presence of 500 nM unlabeled hMCH. Beads were coated with membranes for 20 minutes and dispensed to the 96 wells, various concentrations of test compounds in DMSO were added (final DMSO concentration 1%-2%), then 25 nCi of $[^{125}I]$-$[Phe^{13}Tyr^{19}]$-hMCH (~2000 Ci/mmol; NEN Life Sciences, Boston, Mass.) was added to the wells. After equilibrating at room temperature for 3 hours, the plates were read in a TopCount (Packard, Meriden, Conn.). $IC_{50}$ calculations were performed using Prism 3.0 (GraphPad. Software, San Diego, Calif.). The $IC_{50}$ values were measured in three different experiments.

Example 4

Aeguorin Bioluminescence Functional Assay

The aequorin bioluminescence assay is a reliable test for identifying G-protein-coupled receptors that couple through the G protein subunit family consisting of $G_q$ and $G_{11}$. $G_q$ and $G_{11}$ coupling leads to the activation of phospholipase C, mobilization of intracellular calcium, and activation of protein kinase C.

Stable cell lines expressing either the MCH-1R or the MCH-2R and the aequorin reporter protein were used. The assay was performed using a Luminoskan RT luminometer (Labsystems Inc., Gaithersburg, Md.) controlled by custom software written for a Macintosh PowerPC 6100. 293AEQ17/MCH-1R (or MCH-2R) cells were cultured for 72 hours and the apo-aequorin in the cells was charged for 1 hour with coelenterazine (10 μM) under reducing conditions (300 M reduced glutathione) in ECB buffer (140 mM NaCl, 20 mM KCl, 20 mM HEPES-NaOH, pH 7.4, 5 mM glucose, 1 mM $MgCl_2$, 1 mM $CaCl_2$, 0.1 mg/mL bovine serum albumin).

The cells were harvested, washed once in ECB medium, and resuspended to 500,000 cells/mL. 100 μL of cell suspension (corresponding to $5\times10^4$ cells) was then injected into the test plate containing the hMCH peptides, and the integrated light emission was recorded over 30 seconds, in 0.5-s units. 20 μL of lysis buffer (0.1% final Triton X-100 concentration) was then injected and the integrated light emission recorded over 10 seconds, in 0.5-s units. The "fractional response" values for each well were calculated by taking the ratio of the integrated response to the initial challenge to the total integrated luminescence including the Triton X-100 lysis response.

Example 5

Position 6 Modifications

Human MCH analogs modified in position 6 were prepared by solid-sis phase synthesis and evaluated using the techniques described Examples 1-4. Binding and functional data for analogs of Ac-hMCH(6-16)-NH$_2$ modified in position 6 are compiled Tables 1 and 2.

TABLE 1

Position 6 Modification Binding Assay

X$^6$-Cys$^7$-Met$^8$-Leu$^9$-Gly$^{10}$-Arg$^{11}$-Val$^{12}$-Tyr$^{13}$-Arg$^{14}$-Pro$^{15}$-Cys$^{16}$-NH$_2$

| SEQ. ID. NO. | X$^6$ | MCH-1R IC$_{50}$ (nM) | MCH-2R IC$_{50}$ (nM) | Selectivity 2/1 |
|---|---|---|---|---|
| 1 |  | 0.3 | 0.5 | 1 |
| 2 | Ac-Arg | 1.4 | 2 | 3 |
| 3 | Gva | 0.4 | 12 | 30 |
| 4 | D-Arg | 035 | 47 | 130 |
| 5 | Ac-D-Arg | 0.25 | 650 | 2600 |
| 6 | Ac-D-Ala | 0.77 | 2700 | 3500 |
| 7 | Ac-D-Nle | 4 | 1460 | 370 |
| 8 | Ac-D-Pro | 1.6 | 1260 | 790 |
| 9 | Ac-D-Phe | 0.9 | 1250 | 1380 |
| 10 | Ac-D-Asn | 5.8 | 4040 | 700 |
| 11 | Ac-D-Ser | 0.7 | 3000 | 4700 |
| 12 | Ac-D-Glu | 16 | 6900 | 430 |
| 13 | Ac-D-Lys | 0.3 | 1030 | 3800 |
| 14 | Ac-D-Cit | 3 | 134 | 43 |
| 15 | Δ(X$^6$-Cys$^7$), Mpr$^7$ | 7 | 3500 | 500 |

"2/1" refers to the MCH-2R/MCH-1R IC$_{50}$ binding ratio.
SEQ. ID. NO. 1 is human MCH.
"Gva" refers to des-amino-arginine (5-guanidinovaleric acid).
"Mpr" refers to des-amino-cysteine (3-mercaptopropionic acid).
"Cit" refers to citrulline.
"Nle" refers to norleucine.

Omission of Ac and the amino group of Arg$^6$, e.g. incorporation of 5-guanidino-valeric acid (des-amino-arginine) in position 6, produced the compound of SEQ. ID. NO. 3. SEQ. ID. NO. 3 was not a fully effective agonist at hMCH-1R (49% activation at 10 μM concentration), but it was a full agonist at hMCH-2R of potency similar to that of the parent compound. In contrast the SEQ. ID. NO. 4 analog lacking an Ac group and containing a D-Arg in position 6 was equipotent to Ac-hMCH(6-16)-NH$_2$ at hMCH-1R, but at hMCH-2R was more than 10-fold weaker.

Compounds of SEQ. ID. NOs. 6-13 provided D-enantiomers of hydrophobic amino acids, Ala, Nle, Pro and Phe, and hydrophilic amino acids, Asn, Ser, Glu and Lys, in position 6 of hMCH(6-16)-NH$_2$. These peptides were efficient binders to hMCH-1R but their signal transduction efficacies at the same receptor were more than 10-fold lower than that of Ac-hMCH(6-16)-NH$_2$. However, these compounds poorly bound to and activated hMCH-2R, thus indicating that they were more selective for hMCH-1R.

Replacement of Arg$^6$ with D-enantiomer of yet another hydrophilic amino acid—citrulline, yielded SEQ. ID. NO. 14. SEQ. ID. NO. 14 had a binding affinity for hMCH-1R about 30-fold lower than that of the D-Arg$^6$ compound. At both receptors, agonist potencies of SEQ. ID. NO. 14 with the urea side chain in position 6 were lower than those of the L-Arg$^6$ compound.

In the analog SEQ. ID. NO. 15, the Ac-Arg$^6$ segment of Ac-hMCH(6-16)-NH$_2$ was eliminated and 3-thio-propionic acid (des-amino-cysteine) was used instead of Cys to form the disulfide ring. SEQ. ID. NO. 15 showed about 5-fold lower binding affinity and 30-fold lower activity at hMCH-1R than Ac-hMCH(6-16)-NH$_2$. Similarly to the other peptides modified at position 6, SEQ. ID. NO. 15 was a very weak ligand for hMCH-2R (IC$_{50}$ and EC$_{50}$>3000 nM).

TABLE 2

Position 6 Modification Activity Assay

X$^6$-Cys$^7$-Met$^8$-Leu$^9$-Gly$^{10}$-Arg$^{11}$-Val$^{12}$-Tyr$^{13}$-Arg$^{14}$-Pro$^{15}$-Cys$^{16}$-NH$_2$

| SEQ. ID. NO. | X$^6$ | MCH-1R EC$_{50}$ (nM) | MCH-1R Activation % | MCH-2R EC$_{50}$ (nM) | MCH-2R Activation % | Selectivity 2/1 |
|---|---|---|---|---|---|---|
| 1 |  | 30.9 | 100 | 30.7 | 100 | 1 |
| 2 | Ac-Arg | 20 | 99 | 6.2 | 98 | 0.3 |
| 3 | Gva | 44 | 49 | 10 | 102 | 0.2 |
| 4 | D-Arg | 107 | 130 | 55 | 83 | 0.5 |
| 5 | Ac-D-Arg | 36 | 97 | 140 | 83 | 4 |
| 6 | Ac-D-Ala | 160 | 109 | 4900 | 51 | 30 |
| 7 | Ac-D-Nle | 91 | 115 | 590 | 69 | 6.5 |
| 8 | Ac-D-Pro | 78 | 120 | 560 | 82 | 7 |
| 9 | Ac-D-Phe | 66 | 117 | 510 | 79 | 7 |
| 10 | Ac-D-Asn | 260 | 113 | 5900 | 42 | 22 |
| 11 | Ac-D-Ser | 160 | 114 | 6070 | 39 | 38 |
| 12 | Ac-D-Glu | 630 | 100 | 7200 | 20 | 11 |
| 13 | Ac-D-Lys | 94 | 130 | 2100 | 55 | 22 |
| 14 | Ac-D-Cit | 920 | 91 | 310 | 68 | 0.3 |
| 15 | Δ(X$^6$-Cys$^7$), Mpr$^7$ | 610 | 92 | 3100 | 47 | 5 |

"2/1" refers to the MCH-2R/MCH-1R EC$_{50}$ activity ratio.
SEQ. ID. NO. 1 is human MCH.
"Gva" refers to des-amino-arginine (5-guanidinovaleric acid).
"Mpr" refers to des-amino-cysteine (3-mercaptopropionic acid).
"Cit" refers to citrulline.
"Nle" refers to norleucine.

Example 6

Position 10 Modifications

Human MCH analogs modified in position 10 were prepared by solid-phase synthesis and evaluated using the techniques described Examples 14. The disulfide cycle of Ac-hMCH(6-16)-NH$_2$ encompasses Gly in position 10. Considerable conformational freedom of Gly, in the absence of a constraining side chain, frequently facilitates formation of new peptide conformers (reversed turns). In order to stabilize some of these low-energy conformations of biological significance, Gly is frequently replaced with sterically constraining amino acids such as α-amino acids. Binding and functional data for analogs of Ac-hMCH(6-16)-NH$_2$ modified in position 10 are compiled in Tables 3 and 4.

TABLE 3

Position 10 Modification Binding Assay

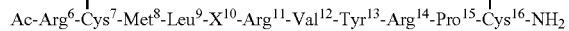

Ac-Arg$^6$-Cys$^7$-Met$^8$-Leu$^9$-X$^{10}$-Arg$^{11}$-Val$^{12}$-Tyr$^{13}$-Arg$^{14}$-Pro$^{15}$-Cys$^{16}$-NH$_2$

| SEQ. ID. NO. | X$^{10}$ | MCH-1R IC$_{50}$ (nM) | MCH-2R IC$_{50}$ (nM) | Selectivity 2/1 |
|---|---|---|---|---|
| 1 |  | 0.3 | 0.5 | 1 |
| 2 | Gly | 0.5 | 2 | 4 |
| 16 | Ala | 0.44 | 7 | 16 |
| 17 | Leu | 0.03 | 27 | 1900 |

TABLE 3

Position 10 Modification Binding Assay

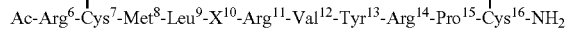

Ac-Arg$^6$-Cys$^7$-Met$^8$-Leu$^9$-X$^{10}$-Arg$^{11}$-Val$^{12}$-Tyr$^{13}$-Arg$^{14}$-Pro$^{15}$-Cys$^{16}$-NH$_2$

| SEQ. ID. NO. | X$^{10}$ | MCH-1R IC$_{50}$ (nM) | MCH-2R IC$_{50}$ (nM) | Selectivity 2/1 |
|---|---|---|---|---|
| 18 | Nle | 0.1 | 1.9 | 21 |
| 19 | Cha | 5 | 55 | 11 |
| 20 | Phe | 0.1 | 1.9 | 19 |
| 21 | Nal(2') | 1.3 | 18 | 14 |
| 22 | Pro | 760 | 3500 | 5 |
| 23 | Arg | 640 | 420 | 0.7 |
| 24 | Lys | 17 | 1460 | 86 |
| 25 | Asn | 0.28 | 490 | 1800 |
| 26 | Ser | 0.54 | 55 | 100 |
| 27 | Cit | 3.1 | 130 | 42 |
| 28 | Glu | 290 | 75%@10 |  |

"2/1" refers to the MCH-2R/MCH-1R IC$_{50}$ binding ratio.
SEQ. ID. NO. 1 is human MCH.
"Cha" refers to 2-cyclohexylalanine.
"Nal(2')" refers to 2'-naphthylalanine.
"Cit" refers to citrulline.
"Nle" refers to norleucine.

TABLE 4

Position 10 Modification Activity Assay

Ac-Arg$^6$-Cys$^7$-Met$^8$-Leu$^9$-X$^{10}$-Arg$^{11}$-Val$^{12}$-Tyr$^{13}$-Arg$^{14}$-Pro$^{15}$-Cys$^{16}$-NH$_2$

| SEQ. ID. NO. | X$^{10}$ | MCH-1R EC$_{50}$ (nM) | MCH-1R Activation % | MCH-2R EC$_{50}$ 2/1 | MCH-2R Activation % | Selectivity 2/1 |
|---|---|---|---|---|---|---|
| 1 |  | 30.9 | 100 | 30.7 | 100 | 1 |
| 2 | Gly | 20 | 99 | 6.2 | 98 | 4.6 |
| 16 | Ala | 51 | 121 | 15 | 102 | 0.29 |
| 17 | Leu | 32 | 123 | 57 | 74 | 1.8 |
| 18 | Nle | 47 | 115 | 17 | 97 | 0.4 |
| 19 | Cha | 1200 | 76 | 300 | 74 | 0.25 |
| 20 | Phe | 66 | 75 | 50 | 88 | 0.75 |
| 21 | Nal(2') | >10000 | 7 | 81 | 105 |  |
| 22 | Pro | >10000 | 10 | >10000 | 13 |  |
| 23 | Arg | >10000 | 7 | 1660 | 38 |  |
| 24 | Lys | 5700 | 43 | 6050 | 40 | 1 |
| 25 | Asn | 51 | 126 | 240 | 86 | 4.7 |
| 26 | Ser | 130 | 120 | 89 | 87 | 0.7 |
| 27 | Cit | 920 | 91 | 310 | 68 | 0.3 |
| 28 | Glu | >10000 | 21 | >10000 | 22 |  |

"2/1" refers to the MCH-2R/MCH-1R EC$_{50}$ activity ratio.
SEQ. ID. NO. 1 is human MCH.
"Cha" refers to 2-cyclohexylalanine.
"Nal(2')" refers to 2'-naphthylalanine.
"Cit" refers to citrulline.
"Nle" refers to norleucine.

Replacement of Gly$^{10}$ with hydrophobic L-amino acids which possess long, branch or aromatic side chains yielded compounds of SEQ. ID. NOs. 16-21. These analogs bound to hMCH-1R almost as efficiently as the parent compound. At hMCH-2R peptides with Leu, Cha and Nal(2') in position 10 (SEQ. ID. NOs. 17, 19, and 21) were 10- to 70-fold weaker binders. At hMCH-1R, signal transduction efficacies of compounds of SEQ. ID. NOs. 16-18, 20 and 21 were similar to that of Ac-hMCH(6-16)-NH$_2$, whereas, at hMCH-2R, these compounds were 5 to 10 times less potent. The Cha$^{10}$ analog with the bulky branched side chain in position 10 (SEQ. ID. NO. 19) poorly activated both receptors. Incorporation of the conformationally constraining Pro in place of Gly$^{10}$ was deleterious to agonism at the hMCH receptors; the Pro$^{10}$ analog was virtually inactive at micromolar concentrations (SEQ. ID. NO. 22).

In compounds of SEQ. ID. NOs. 23-27 hydrophilic residues were incorporated in position 10. Peptides with Asn, Ser, Cit and Lys in position 10 were high affinity binders to hMCH-1R, but their affinities for hMCH-2R were 30 to 700 times lower than that of Ac-hMCH(6-16)NH$_2$. Also, the Asn$^{10}$, Ser$^{10}$ and Cit$^{10}$ peptides were from 3 to 50-fold weaker agonists at both hMCH receptors than the parent compound, and the Lys$^{10}$ analog was 300 times less potent. The SEQ. ID. NO. 28 analog with an acidic residue in position 10, the Glu$^{10}$ peptide, was practically inactive at hMCH-1R and hMCH-2R.

Example 7

Multiple Modifications

Human MCH analogs modified at least in positions 6 and 10 were prepared by solid-phase synthesis and evaluated using the techniques described in Examples 1-4. Binding and functional data for analogs of Ac-hMCH(6-16)-NH$_2$ modified in at least positions 6 and 10 are compiled in Tables 5 and 6.

TABLE 5

Multiple Modifications Binding Assay

Ac-Arg⁶-Cys⁷-Met⁸-Leu⁹-Gly¹⁰-Arg¹¹-Val¹²-Tyr¹³-Arg¹⁴-Pro¹⁵-Cys¹⁶-NH₂

| SEQ. ID. NO. | Modification | MCH-1R IC$_{50}$ (nM) | MCH-2R IC$_{50}$ (nM) | Selectivity 2/1 |
|---|---|---|---|---|
| 1 |  | 0.3 | 0.5 | 1 |
| 2 |  | 0.5 | 2 | 4 |
| 29 | D-Arg⁶-Asn¹⁰ | 0.5 | 3300 | 6600 |
| 30 | D-Arg⁶-Gln¹⁰ | 6.1 | 1400 | 230 |
| 31 | D-Arg⁶-Nle⁸, Asn¹⁰ | 0.28 | 1600 | 5700 |
| 32 | ΔAc,D-Arg⁶, Nle⁸, Asn¹⁰ | 0.09 | 250 | 890 |
| 33 | D-Arg⁶, Asn¹⁰, Ala¹⁴ | 3.2 | 48%@10 |  |
| 34 | D-Cit⁶, Asn¹⁰ | 8.3 | 55%@10 |  |

"2/1" refers to the MCH-2R/MCH-1R IC$_{50}$ binding ratio.
SEQ. ID. NO. 1 is human MCH.
"Cit" refers to citrulline.
"Nle" refers to norleucine.

TABLE 6

Multiple Modifications

Ac-Arg⁶-Cys⁷-Met⁸-Leu⁹-Gly¹⁰-Arg¹¹-Val¹²-Tyr¹³-Arg¹⁴-Pro¹⁵-Cys¹⁶-NH₂

| SEQ. ID. NO. | Modification | MCH-1R EC$_{50}$ (nM) | MCH-1R Activation % | MCH-2R EC$_{50}$ (nM) | MCH-2R Activation % | Selectivity 2/1 |
|---|---|---|---|---|---|---|
| 1 |  | 30.9 | 100 | 30.7 | 100 | 1 |
| 2 |  | 20 | 99 | 6.2 | 98 | 0.3 |
| 29 | D-Arg⁶-Asn¹⁰ | 55 | 120 | 8400 | 20 | 150 |
| 30 | D-Arg⁶-Gln¹⁰ | 2300 | 74 | >10000 | 11 |  |
| 31 | D-Arg⁶, Nle⁸, Asn¹⁰ | 240 | 130 | 5500 | 23 | 23 |
| 32 | ΔAc, D-Arg⁶, Nle⁸, Asn¹⁰ | 350 | 130 | 1470 | 53 | 4 |
| 33 | D-Arg⁶, Asn¹⁰, Ala¹⁴ | 260 | 109 | >10000 | 17 |  |
| 34 | D-Cit⁶, Asn¹⁰ | 1460 | 110 | >10000 | 8 |  |

"2/1" refers to the MCH-2R/MCH-1R EC$_{50}$ activity ratio.
SEQ. ID. NO. 1 is human MCH.
"Cit" refers to citrulline.
"Nle" refers to norleucine.

SEQ. ID. NOs. 29-34 were designed to incorporate changes in the structure of Ac-hMCH(6-16)NH₂ favorable for hMCH-1R selectivity. The D-Arg⁶, Asn¹⁰ and D-Arg⁶, Gln¹⁰ analogs, SEQ. ID. NOs. 29 and 30 activated hMCH-1R almost as efficiently as Ac-hMCH(6-16)NH₂. They were about 150-fold more selective as agonists for hMCH-1R than hMCH-2R. In SEQ. ID. NOs. 31 and 32 Met⁸ was replaced with the isosteric Nle. These analogs were potent and selective hMCH-1R agonists.

Omission of the guanidino group in position 14 in Ac-hMCH(6-16)-NH₂, through the replacement of Arg with Ala, yielded SEQ. ID. NO. 33. The SEQ. ID. NO. 33 compound was a 5-fold weaker agonist at hMCH-1R receptor than the parent compound, but was about 50-fold more selective with respect to hMCH-2R.

Other embodiments are within the following claims. While several embodiments have been shown and described, various modifications may be made without departing from the spirit and scope of the present invention.

What is claimed is:

1. A peptide consisting of the structure:

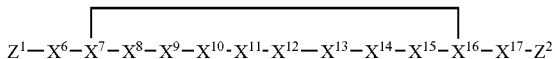

wherein $X^6$ is selected from the group consisting of: D-arginine, D-alanine, D-norleucine, D-α-aminobutyric acid, D-valine, D-leucine, D-isoleucine, D-proline, D-methionine, D-phenylalanine, D-asparagine, D-glutamine, D-serine, D-threonine, D-glutamic acid, D-aspartic acid, D-lysine, D-histidine, D-tryptophan, D-tyrosine, D-cyclohexylalanine, D-(2')naphthylalanine, D-ornithine, D-homoarginine, D-nitroarginine, D-norarginine and D-citrulline, $X^7$ is cysteine, $X^8$ is either methionine, norleucine, or N-methyl norleucine, $X^9$ is leucine, $X^{10}$ is either asparagine, glutamine, leucine, isoleucine, valine, norleucine, cyclohexylalanine, phenylalanine, (2')-naphthylalanine, tyrosine, histidine, tryptophan, lysine, serine, threonine, methionine, or citrulline, $X^{11}$ is arginine, $X^{12}$ is valine, $X^{13}$ is phenylalanine, (2')napthylalanine, p-fluoro-phenylalanine, tyrosine, or cyclohexylalanine, $X^{14}$ is arginine or alanine, $X^{15}$ is either proline or sarcosine, $X^{16}$ is cysteine or D-cysteine, $X^{17}$ is an optionally present amino acid that, if present, is either tryptophan or tyrosine, $Z^1$ is an optionally present protecting group that, if present, is covalently joined to the N-terminal amino group, $Z^2$ is an optionally present protecting group that, if present, is covalently joined to the C-terminal carboxy group, and wherein said peptide optionally contains a detectable label, or a pharmaceutically acceptable salt of said peptide.

2. The peptide of claim 1, wherein said detectable label is a luminescent label, an enzymatic label or a radiolabel.

3. The peptide of claim 2, wherein $X^6$ is either D-arginine, D-alanine, D-norleucine, D-proline, D-phenylalanine, D-asparagine, D-serine, D-glutamic acid, D-lysine, or D-citrulline.

4. The peptide of claim 3, wherein $X^{10}$ is glutamine.

5. The peptide of claim 4, wherein said peptide is substituted with a radiolabel.

6. The peptide of claim 4, wherein said peptide is not substituted with a radiolabel.

7. The peptide of claim 4, wherein $X^{17}$ is not present, $Z^1$ is —C(O)CH$_3$ and $Z^2$ is —NH$_2$.

8. The peptide of claim 1, wherein said detectable label is not present.

9. The peptide of claim 8, wherein $X^{17}$ is not present, $Z^1$ is —C(O)CH$_3$ and $Z^2$ is —NH$_2$.

10. The peptide of claim 1, wherein said peptide consists of a sequence selected from the group consisting of: SEQ ID NOs: 29, 30, 31, 32, 33, and 34.

11. The peptide of claim 1, wherein said peptide consists of SEQ ID NO: 30.

12. A method of screening for a compound able to bind MCH-1R comprising the step of measuring the ability of said compound to inhibit binding of a peptide of claim 1 to MCH-1R, wherein said compound that inhibits binding of the peptide to MCH-1R is identified as able to bind MCH-1R.

13. The method of claim 12, wherein said peptide is radiolabeled.

* * * * *

SEQUENCE LISTING

<160> NUMBER OF SEQ ID NOS: 38

<210> SEQ ID NO 1
<211> LENGTH: 19
<212> TYPE: PRT
<213> ORGANISM: Human
<220> FEATURE:
<221> NAME/KEY: DISULFID
<222> LOCATION: (7)...(16)

<400> SEQUENCE: 1

Ala Phe Asp Met Leu Arg Cys Met Leu Gly Arg Val Tyr Arg Pro Cys
 1               5                  10                  15

Trp Gln Val

<210> SEQ ID NO 2
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 2

Arg Cys Met Leu Gly Arg Val Tyr Arg Pro Cys
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = des-amino-arginine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 3

Xaa Cys Met Leu Gly Arg Val Tyr Arg Pro Cys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: DISULFID
<222> LOCATION: (2)...(11)

```
<220> FEATURE:
<221> NAME/KEY: AMIDATION
<222> LOCATION: (11)...(11)

<400> SEQUENCE: 4

Xaa Cys Met Leu Gly Arg Val Tyr Arg Pro Cys
 1               5                   10

<210> SEQ ID NO 5
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 5

Xaa Cys Met Leu Gly Arg Val Tyr Arg Pro Cys
 1               5                   10

<210> SEQ ID NO 6
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-alanine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 6

Xaa Cys Met Leu Gly Arg Val Tyr Arg Pro Cys
 1               5                   10

<210> SEQ ID NO 7
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-norleucine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
```

```
<221> NAME/KEY: AMIDATION
<222> LOCATION: (11)...(11)

<400> SEQUENCE: 7

Xaa Cys Met Leu Gly Arg Val Tyr Arg Pro Cys
 1               5                   10

<210> SEQ ID NO 8
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-proline
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 8

Xaa Cys Met Leu Gly Arg Val Tyr Arg Pro Cys
 1               5                   10

<210> SEQ ID NO 9
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-phenylalanine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 9

Xaa Cys Met Leu Gly Arg Val Tyr Arg Pro Cys
 1               5                   10

<210> SEQ ID NO 10
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-asparagine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
```

```
<222> LOCATION: (11)...(11)

<400> SEQUENCE: 10

Xaa Cys Met Leu Gly Arg Val Tyr Arg Pro Cys
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-serine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 11

Xaa Cys Met Leu Gly Arg Val Tyr Arg Pro Cys
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-glutamine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 12

Xaa Cys Met Leu Gly Arg Val Tyr Arg Pro Cys
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-lysine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
```

```
<400> SEQUENCE: 13

Xaa Cys Met Leu Gly Arg Val Tyr Arg Pro Cys
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-citrulline
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 14

Xaa Cys Met Leu Gly Arg Val Tyr Arg Pro Cys
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = des-amino-cysteine
<220> FEATURE:
<221> NAME/KEY: AMIDATION
<222> LOCATION: (10)...(10)

<400> SEQUENCE: 15

Xaa Met Leu Gly Arg Val Tyr Arg Pro Cys
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 16

Arg Cys Met Leu Ala Arg Val Tyr Arg Pro Cys
 1               5                  10

<210> SEQ ID NO 17
<211> LENGTH: 11
<212> TYPE: PRT
<213> ORGANISM: Artificial Sequence
```

```
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 17

Arg Cys Met Leu Leu Arg Val Tyr Arg Pro Cys
 1               5                   10

<210> SEQ ID NO 18
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (5)...(5)
<223> OTHER INFORMATION: Xaa = norleucine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 18

Arg Cys Met Leu Xaa Arg Val Tyr Arg Pro Cys
 1               5                   10

<210> SEQ ID NO 19
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (5)...(5)
<223> OTHER INFORMATION: Xaa = 2-cyclohexylalanine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 19

Arg Cys Met Leu Xaa Arg Val Tyr Arg Pro Cys
 1               5                   10

<210> SEQ ID NO 20
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
```

```
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 20

Arg Cys Met Leu Phe Arg Val Tyr Arg Pro Cys
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (5)...(5)
<223> OTHER INFORMATION: Xaa = 2'-naphthylalanine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 21

Arg Cys Met Leu Xaa Arg Val Tyr Arg Pro Cys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 22

Arg Cys Met Leu Pro Arg Val Tyr Arg Pro Cys
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 23
```

```
Arg Cys Met Leu Arg Arg Val Tyr Arg Pro Cys
 1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 24

```
Arg Cys Met Leu Lys Arg Val Tyr Arg Pro Cys
 1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 25

```
Arg Cys Met Leu Asn Arg Val Tyr Arg Pro Cys
 1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 26

```
Arg Cys Met Leu Ser Arg Val Tyr Arg Pro Cys
 1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (5)...(5)

```
<223> OTHER INFORMATION: Xaa = citrulline
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 27

Arg Cys Met Leu Xaa Arg Val Tyr Arg Pro Cys
 1               5                   10

<210> SEQ ID NO 28
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 28

Arg Cys Met Leu Glu Arg Val Tyr Arg Pro Cys
 1               5                   10

<210> SEQ ID NO 29
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 29

Xaa Cys Met Leu Asn Arg Val Tyr Arg Pro Cys
 1               5                   10

<210> SEQ ID NO 30
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: DISULFID
<222> LOCATION: (2)...(11)
<220> FEATURE:
```

<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 30

Xaa Cys Met Leu Gln Arg Val Tyr Arg Pro Cys
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: MOD_RES
<222> LOCATION: (3)...(3)
<223> OTHER INFORMATION: Xaa = norleucine
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 31

Xaa Cys Xaa Leu Asn Arg Val Tyr Arg Pro Cys
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine
<220> FEATURE:
<221> NAME/KEY: MOD_RES
<222> LOCATION: (3)...(3)
<223> OTHER INFORMATION: Xa= norleucine
<220> FEATURE:
<221> NAME/KEY: DISULFID
<222> LOCATION: (2)...(11)
<220> FEATURE:
<221> NAME/KEY: AMIDATION
<222> LOCATION: (11)...(11)

<400> SEQUENCE: 32

Xaa Cys Xaa Leu Asn Arg Val Tyr Ala Pro Cys
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = D-arginine

```
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 33

Xaa Cys Met Leu Asn Arg Val Tyr Ala Pro Cys
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: MCH Analog
<220> FEATURE:
<221> NAME/KEY: MOD_RES
<222> LOCATION: (1)...(1)
<223> OTHER INFORMATION: Xaa = citrulline
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 34

Xaa Cys Met Leu Asn Arg Val Thr Arg Pro Cys
 1               5                  10

<210> SEQ ID NO 35
<211> LENGTH: 353
<212> TYPE: PRT
<213> ORGANISM: Human

<400> SEQUENCE: 35

Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
                20                  25                  30

Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
        50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160
```

```
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
            260                 265                 270
Tyr Val Leu Gln Leu Thr Gln Leu Ser Ile Ser Arg Pro Thr Leu Thr
        275                 280                 285
Phe Val Tyr Leu Tyr Asn Ala Ala Ile Ser Leu Gly Tyr Ala Asn Ser
    290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Ala
                325                 330                 335
Val Ser Asn Ala Gln Thr Ala Asp Glu Glu Arg Thr Glu Ser Lys Gly
            340                 345                 350
Thr

<210> SEQ ID NO 36
<211> LENGTH: 1062
<212> TYPE: DNA
<213> ORGANISM: Human

<400> SEQUENCE: 36
atggacctgg aagcctcgct gctgcccact ggtcccaacg ccagcaacac ctctgatggc      60
cccgataacc tcacttcggc aggatcacct cctcgcacgg ggagcatctc ctacatcaac     120
atcatcatgc cttcggtgtt cggcaccatc tgcctcctgg gcatcatcgg aactccacg      180
gtcatcttcg cggtcgtgaa gaagtccaag ctgcactggt gcaacaacgt ccccgacatc     240
ttcatcatca acctctcggt agtagatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccactgtcca ccccatctct tccacgaagt ccggaagcc ctctgtggcc      480
accctggtga tctgcctcct gtgggccctc tccttcatca gcatcacccc tgtgtggctg     540
tatgccagac tcatccccct tccaggaggt gcagtgggct gcggcatacg cctgcccaac     600
ccagacactg acctctactg gttcaccctg taccagtttt tcctggcctt tgccctgcct     660
tttgtggtca tcacagccgc atacgtgagg atcctgcagc gcatgacgtc ctcagtggcc     720
cccgcctccc agcgcagcat ccggctgcgg acaaagaggg tgacccgcac agccatcgcc     780
atctgtctgg tcttctttgt gtgctgggca ccctactatg tgctacagct gacccagttg     840
tccatcagcc gccgacccct cacctttgtc tacttataca atgcggccat cagcttgggc     900
tatgccaaca gctgcctcaa ccccttttgtg tacatcgtgc tctgtgagac gttccgcaaa     960
cgcttggtcc tgtcggtgaa gcctgcagcc caggggcagc ttcgcgctgt cagcaacgct    1020
```
cagacggctg acgaggagag gacagaaagc aaaggcacct ga                    1062

<210> SEQ ID NO 37
<211> LENGTH: 340
<212> TYPE: PRT
<213> ORGANISM: Human

<400> SEQUENCE: 37

Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340

<210> SEQ ID NO 38

-continued

```
<211> LENGTH: 1023
<212> TYPE: DNA
<213> ORGANISM: Human

<400> SEQUENCE: 38
atgaatccat ttcatgcatc ttgttggaac acctctgccg aacttttaaa caaatcctgg      60
aataaagagt ttgcttatca aactgccagt gtggtagata cagtcatcct cccttccatg     120
attgggatta tctgttcaac agggctggtt ggcaacatcc tcattgtatt cactataata     180
agatccagga aaaaacagt  ccctgacatc tatatctgca acctggctgt ggctgatttg     240
gtccacatag ttggaatgcc ttttcttatt caccaatggg cccgagggg  agagtgggtg     300 tttgggggc  ctctctgcac catcatcaca tccctggata cttgtaacca atttgcctgt     360
agtgccatca tgactgtaat gagtgtggac aggtactttg ccctcgtcca accatttcga     420
ctgacacgtt ggagaacaag gtacaagacc atccggatca atttgggcct ttgggcagct     480
tcctttatcc tggcattgcc tgtctgggtc tactcgaagg tcatcaaatt taaagacggt     540
gttgagagtt gtgcttttga tttgacatcc cctgacgatg tactctggta tacactttat     600
ttgacgataa caacttttt  tttccctcta cccttgattt tggtgtgcta tattttaatt     660
ttatgctata cttgggagat gtatcaacag aataaggatg ccagatgctg caatcccagt     720
gtaccaaaac agagagtgat gaagttgaca aagatggtgc tggtgctggt ggtagtcttt     780
atcctgagtg ctgccccta  tcatgtgata caactggtga acttacagat ggaacagccc     840
acactggcct tctatgtggg ttattacctc tccatctgtc tcagctatgc cagcagcagc     900
attaaccctt ttctctacat cctgctgagt ggaaatttcc agaaacgtct gcctcaaatc     960
caaagaagag cgactgagaa ggaaatcaac aatatgggaa acactctgaa atcacacttt    1020
tag                                                                  1023
```